United States Patent
Schabbach et al.

(10) Patent No.: US 12,178,993 B2
(45) Date of Patent: Dec. 31, 2024

(54) DISPOSABLE DELIVERY ASSEMBLY FOR A DRUG DELIVERY DEVICE

(71) Applicant: Sanofi-Aventis Deutschland GMBH, Frankfurt am Main (DE)

(72) Inventors: Michael Schabbach, Frankfurt am Main (DE); Olaf Zeckai, Weinheim (DE); Meinolf Werner, Worms (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 135 days.

(21) Appl. No.: 17/679,244

(22) Filed: Feb. 24, 2022

(65) Prior Publication Data

US 2022/0176033 A1 Jun. 9, 2022

Related U.S. Application Data

(63) Continuation of application No. 15/104,837, filed as application No. PCT/EP2014/078410 on Dec. 18, 2014, now Pat. No. 11,260,170.

(30) Foreign Application Priority Data

Dec. 20, 2013 (EP) ..................................... 13198773

(51) Int. Cl.
*A61M 5/142* (2006.01)
*A61M 5/148* (2006.01)
*A61M 5/162* (2006.01)

(52) U.S. Cl.
CPC ........ *A61M 5/148* (2013.01); *A61M 5/14232* (2013.01); *A61M 5/14244* (2013.01);
(Continued)

(58) Field of Classification Search
CPC ......... A61M 2005/14252; A61M 2005/14268; A61M 5/14244; A61M 5/14248; A61M 5/162
See application file for complete search history.

(56) References Cited

U.S. PATENT DOCUMENTS 3,384,080 A * 5/1968 Muller ................ F04B 43/1253
                                                                 417/328
6,595,956 B1 * 7/2003 Gross .................... A61M 5/158
                                                                 604/141
(Continued)

FOREIGN PATENT DOCUMENTS

CN           103118737        5/2013
WO        WO 2005/037350      4/2005
(Continued)

OTHER PUBLICATIONS

International Preliminary Report on Patentability in International Application No. PCT/EP2014/078410, dated Jun. 21, 2016, 6 pages.
(Continued)

*Primary Examiner* — James D Ponton
*Assistant Examiner* — Hong-Van N Trinh
(74) *Attorney, Agent, or Firm* — Fish & Richardson P.C.

(57) ABSTRACT

The present invention relates to a disposable delivery assembly for a drug delivery device to dispense a liquid medicament, the delivery assembly comprising:
- a disposable injector comprising an injection needle, a flexible tube and an injector fluid coupling, wherein the injection needle is in fluid communication with the fluid coupling via the flexible tube,
- a disposable cartridge comprising a reservoir at least partially filled with the liquid medicament and comprising a cartridge fluid coupling in fluid communication with the reservoir,
wherein the injector and the cartridge are mechanically interconnected in an undeployed configuration, in which the injector fluid coupling and the cartridge fluid coupling are disconnected, and
(Continued)

wherein the cartridge is displaceable relative to the injector into a deployed configuration, in which the injector fluid coupling and the cartridge fluid coupling are in fluid communication.

16 Claims, 9 Drawing Sheets

(52) U.S. Cl.
CPC ........ *A61M 5/14248* (2013.01); *A61M 5/162* (2013.01); *A61M 2005/14252* (2013.01); *A61M 2005/14256* (2013.01); *A61M 2005/14268* (2013.01)

(56) References Cited

U.S. PATENT DOCUMENTS

2007/0154336 A1  7/2007  Miyazaki et al.
2008/0255516 A1* 10/2008  Yodfat .............. A61M 5/14248
                                                     604/151

FOREIGN PATENT DOCUMENTS

| WO | WO 2006/108809 | 10/2006 |
| WO | WO 2010/029054 | 3/2010 |
| WO | WO 2011/133823 | 10/2011 |
| WO | WO 2013/041702 | 3/2013 |

OTHER PUBLICATIONS

International Search Report and Written Opinion in International Application No. PCT/EP2014/078410, mailed Mar. 6, 2015, 9 pages.

Rote Liste, "50. Hypophysen-, Hypothalamushormone, andere regulatorische Peptide u. ihre Hemmstoffe," Chapter 50, ed. 2008, 20 pages.

* cited by examiner

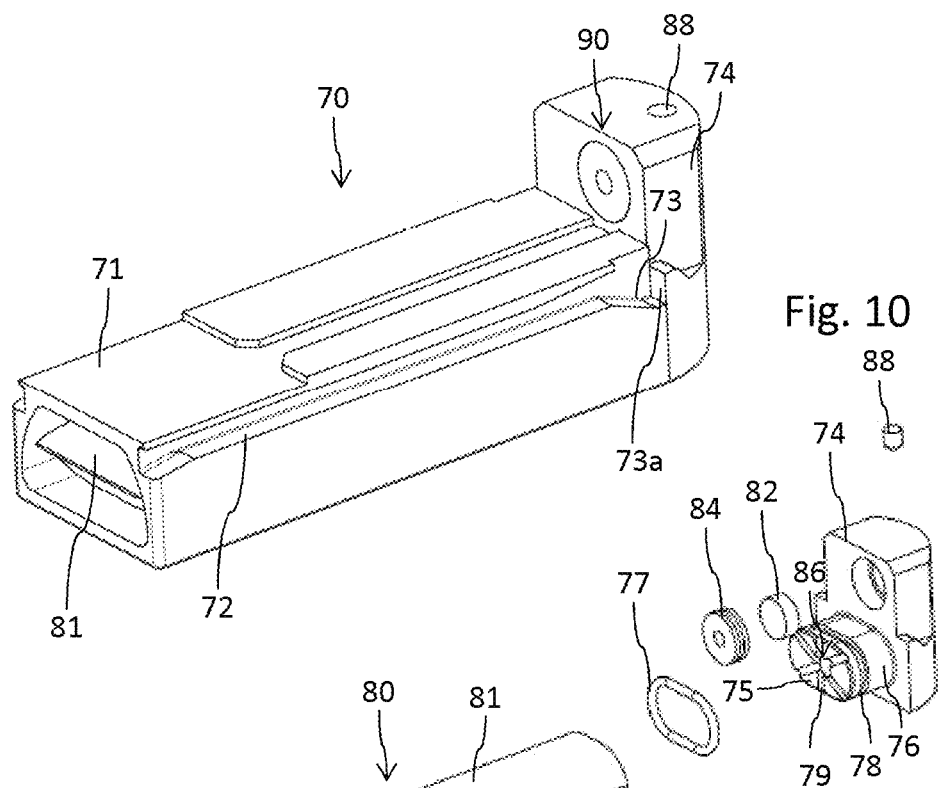
Fig. 10
Fig. 11
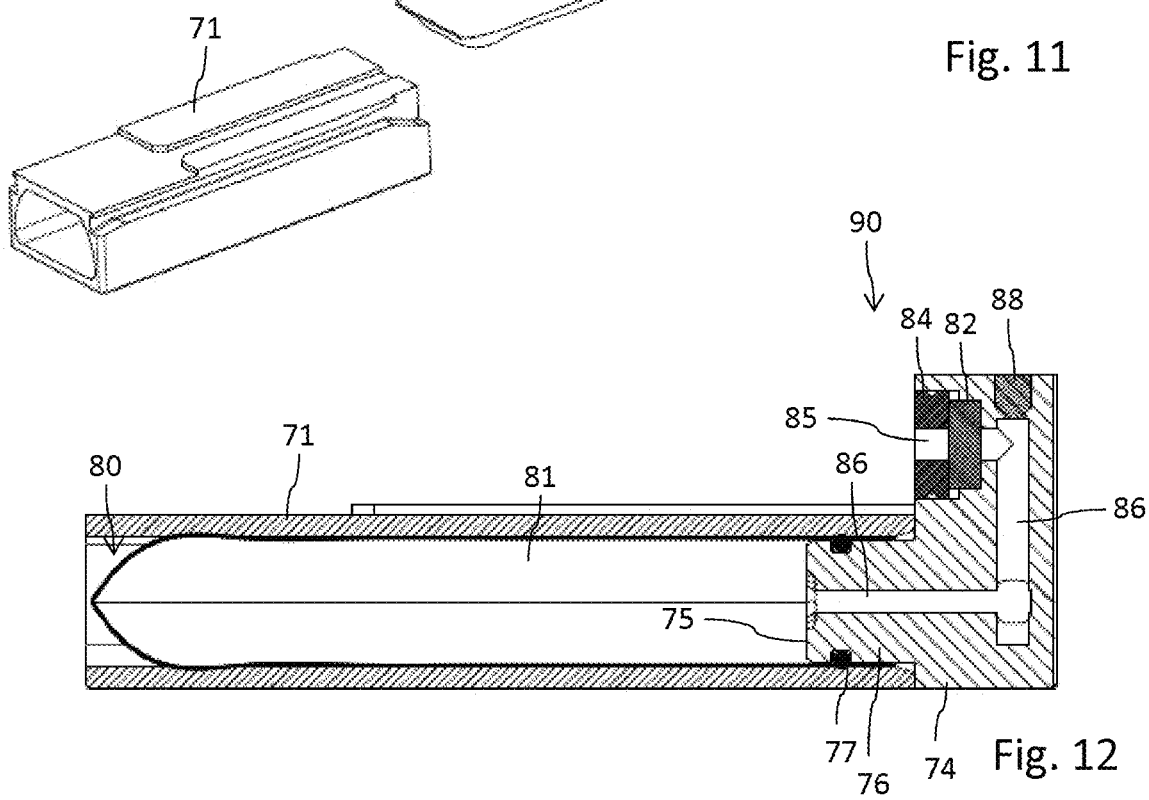
Fig. 12

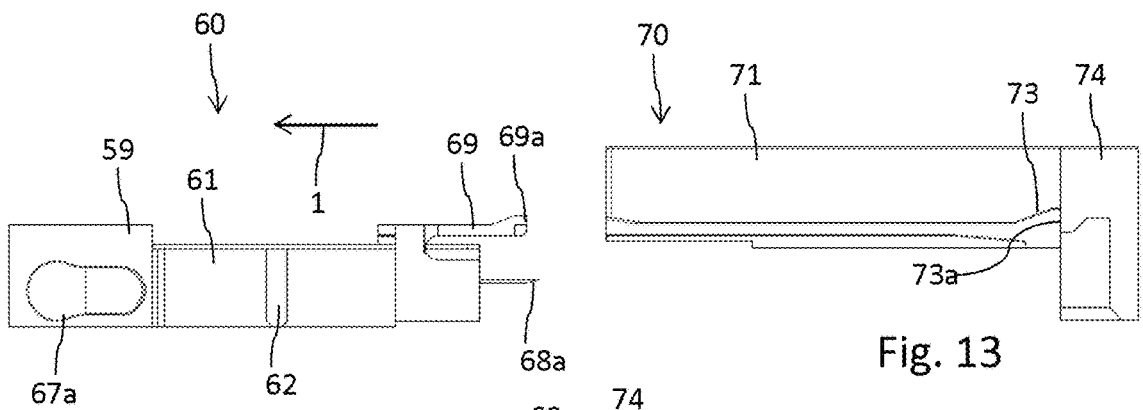
Fig. 13
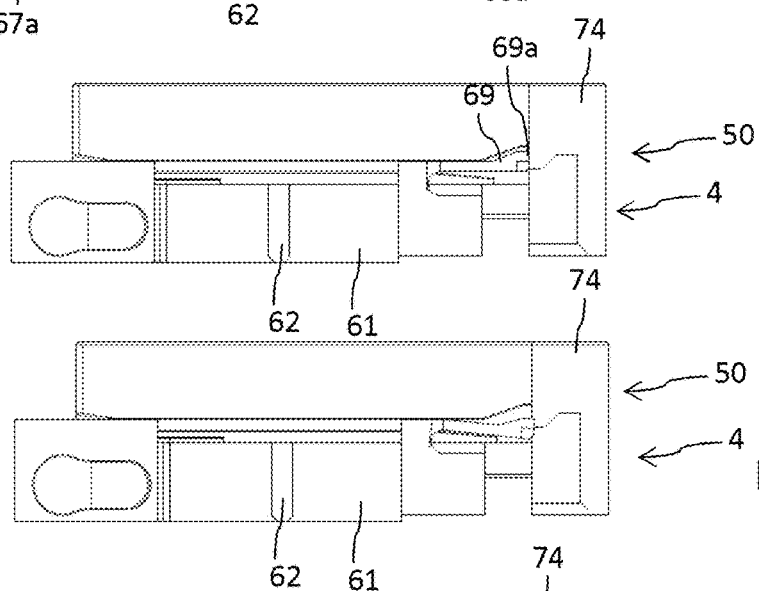
Fig. 14a
Fig. 14b
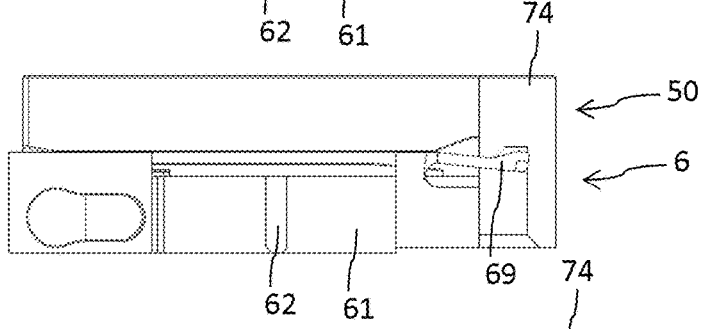
Fig. 14c
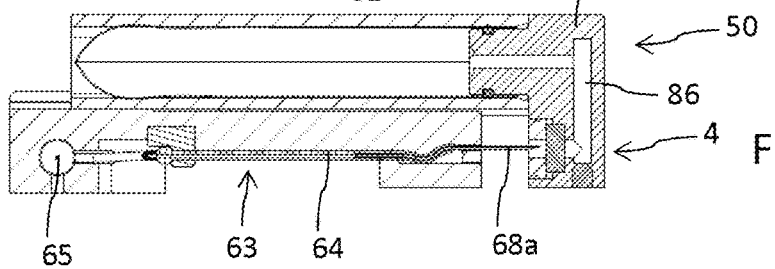
Fig. 15a
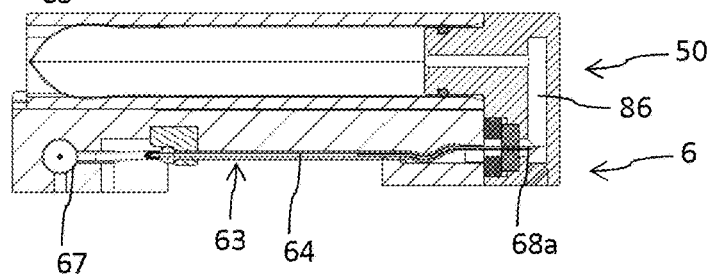
Fig. 15b

DISPOSABLE DELIVERY ASSEMBLY FOR A DRUG DELIVERY DEVICE

CROSS-REFERENCE TO RELATED APPLICATIONS

The present application is a continuation of U.S. patent application Ser. No. 15/104,837, filed on Jun. 15, 2016, which is the national stage entry of International Patent Application No. PCT/EP2014/078410, filed on Dec. 18, 2014, and claims priority to Application No. EP 13198773.7, filed on Dec. 20, 2013, the disclosures of which are incorporated herein by reference.

FIELD OF THE INVENTION

The present invention relates to the field of drug delivery devices and in particular to the field of peristaltic pumps for controlled delivery of a medicament to a patient. In an aspect the invention relates to a disposable delivery assembly to engage and/or to cooperate with such a drug delivery device.

BACKGROUND

Parenteral delivery of liquid medicaments into dermal tissue of a patient may be accomplished by administering bolus injections using a needle and a reservoir, or continuously by appropriate dispensers or transdermal patch technology which may be driven by gravity. Gravity feed systems compromise the patient's mobility and lifestyle and limit the therapy to simplistic flow rates and profiles. Ambulatory infusion pumps have been developed that provide sophisticated fluid delivery profiles accomplishing bolus requirements, continuous infusion and variable flow rate delivery.

Ambulatory pump systems typically include a reservoir containing the liquid medicament and make further use of an injection assembly comprising an injection needle and some kind of tube structure through which the medicament is transported by way of a feeder of the infusion pump.

Document WO 2013/041702 A1 discloses a peristaltic pump comprising a tube for transporting the liquid medicament, wherein the tube is arranged along a longitudinal axis. The peristaltic pump further comprises a rotatable pump head for causing a squeezing of the tube, wherein the pump head is rotatable about a rotation axis. The peristaltic pump further comprises a receptacle that is configured to receive a cartridge or a container holding the material to be transported. With peristaltic pumps featuring a pump head or feeder a rather hermetically sealed fluid path from the cartridge towards an injection needle can be provided such that the pump head or any other fluid feeding component of the peristaltic pump does not get in direct contact with the medicament. In this way, contamination of the medicament by components of the pump as well as contamination of the pump by the medicament can be effectively avoided. For reasons of hygiene as well as for patient safety and patient compliance it is of particular benefit to make use of disposable reservoirs or cartridges containing the medicament as well as to make use of disposable fluid transferring components that have to be replaced from time to time.

A fluid transferring component of such drug delivery systems providing a fluid path from a medicament reservoir towards an injection needle may be denoted as injector in the present context. For hygienic reasons as well as for patient safety and compliance it is desirable to provide a rather easy and intuitive replacement of cartridge and injector. It is a further object to provide a well-defined and smoothly operating fluid transferring mutual coupling of a disposable cartridge and a disposable injector. It would be rather beneficial to establish a fluid transferring coupling between injector and cartridge just immediately before the drug delivery device is initially operated so that a sealed cartridge is not prematurely or unnecessarily coupled with the injector. In this context it would be of further benefit to avoid that liquid medicament already enters the injector and its fluid transferring system, e.g. a fluid transferring tube prior to a delivery operation to be conducted by the drug delivery device.

SUMMARY OF THE INVENTION

In a first aspect a disposable delivery assembly is provided for a drug delivery device. When engaged with the drug delivery device the disposable delivery assembly together with the drug delivery device is operable to dispense a liquid medicament to a patient. The drug delivery device is typically implemented as a delivery pump, in particular as a peristaltic pump but is generally not limited to such particular pump systems. The disposable delivery assembly comprises a disposable cartridge and a disposable injector. Hence, the disposable delivery assembly comprises those components of the drug delivery device that get in direct contact with the liquid medicament.

The disposable injector comprises an injection needle for transdermal piercing of a patient's skin. The disposable injector further comprises a flexible tube and an injector fluid coupling. The flexible tube is adapted and operable to interact with a feeder, in particular with a pump head of the drug delivery device. The injector fluid coupling of the disposable injector is operable and designed to engage with the disposable cartridge in a fluid transferring way. Hence, the injection needle is in fluid communication with the injector fluid coupling via the flexible tube. The disposable injector therefore defines a fluid path extending from the injector fluid coupling through the flexible tube towards the injection needle.

The disposable delivery assembly further comprises a disposable cartridge comprising a reservoir which is at least partially filled with the liquid medicament to be dispensed. The disposable cartridge comprises a cartridge fluid coupling which is in fluid communication with the reservoir. Cartridge fluid coupling and injector fluid coupling mutually complement each other so that cartridge fluid coupling and injector fluid coupling may releasably engage to establish a fluid transfer from the interior of the cartridge to the disposable injector's injection needle.

Injector and cartridge are mechanically interconnected in an undeployed configuration, in which the injector fluid coupling and the cartridge fluid coupling are disconnected. Hence, in the undeployed configuration there is no fluid or medicament transfer from the cartridge to the injector. In the undeployed configuration the disposable delivery assembly is not yet operable to deliver the liquid medicament. Nevertheless, in the undeployed configuration injector and cartridge are mechanically assembled and interconnected to form the disposable delivery assembly.

In the undeployed configuration injector and cartridge are pre-assembled so that a patient or end user making use of the drug delivery device is no longer obliged to separately handle injector and cartridge. The delivery assembly, hence the pre-assembly of injector and cartridge is of particular benefit for patient safety and for hygienic reasons. Mutually corresponding and suitable pairs of disposable injectors and disposable cartridges may be preassembled by a pharmaceutical manufacturer so that a risk of an incorrect mutual assembly of injector and cartridge can be limited or completely eliminated. In addition, general handling and patient compliance can be facilitated and improved. It is particularly conceivable that disposable cartridge and disposable injector are non-detachably interconnected. In this way, replacement of a cartridge also enforces and requires replacement of the injector.

In order to activate a drug delivery procedure cartridge and injector are displaceable relative to each other into a deployed configuration. In the deployed configuration the injector fluid coupling and the cartridge fluid coupling are in fluid communication. Then, the medicament contained in the cartridge can be transported through the injector's tube and towards the injector's injection needle.

It is of particular benefit, when cartridge and injector are exclusively transferable into the deployed configuration by interaction with the drug delivery device. In this way, establishing of a premature fluid transferring coupling of disposable injector and disposable cartridge, e.g. when not assembled to the drug delivery device can be effectively avoided.

It is of further benefit, when injector and cartridge are also transferable from the deployed configuration into the undeployed configuration, e.g. when the content of the cartridge has been used up. Returning of cartridge and injector into the undeployed configuration may be accomplished and supported by the general handling of the drug delivery device upon exchanging or replacing the empty cartridge by a new one. Returning of disposable cartridge and disposable injector into the undeployed configuration may be of particular benefit to avoid droplet generation at a distal, hence at a dispensing end of the injection needle. Contamination of the environment by the medicament upon cartridge replacement can therefore be effectively avoided and counteracted.

In an embodiment the delivery assembly consists of the disposable cartridge and the injector. Hence, the delivery assembly is composed and provided by the mutual coupling and direct mechanical connection of the disposable cartridge and the disposable injector. In this way the delivery assembly is also of disposable type. Even when unconnected from the drug delivery device the delivery assembly provides and forms a single unit which is insertable into a drug delivery device and/or which is connectable to a drug delivery device by a single step of assembly. The delivery assembly is commercially distributable as a single unit, which only upon insertion into or coupling with the drug delivery device is configurable from the undeployed configuration into the deployed configuration. So even when uncoupled from the drug delivery device and when in undeployed configuration disposable cartridge and disposable injector are directly mechanically connected. Hence, they are fastened to each other.

A user of the device only has to handle the single delivery assembly for exchanging the cartridge and/or the injector. This is not only much easier in comparison to a manual assembly and disassembly of disposable injector and disposable cartridge but also enforces and requires a simultaneous replacement of disposable cartridge and disposable injector. In this way the user cannot replace an empty cartridge while continuing using the injector. In this way certain requirements in regard to product contamination can be enhanced and patient safety can be increased.

Moreover the drug delivery device is configured to releasably engage and to releasably connect with the delivery assembly in form of a single unit. Also, a separate arrangement and assembly of the cartridge or of the injector can be prevented in this way.

According to an embodiment one of cartridge and injector comprises at least one stop member engaging with a correspondingly-shaped stop face of the other one of cartridge and injector. In this way, a self-acting displacement of cartridge and injector from the undeployed configuration into the deployed configuration can be impeded. It can be avoided, that cartridge and injector prematurely engage in a fluid transferring way, i.e. prior to an assembly to or in the drug delivery device. The mutual engagement of cartridge and injector via mutually corresponding stop member and stop face avoids that medicament could be dispensed without a predefined interaction or coupling with the drug delivery device.

By means of mutually corresponding stop member and stop face of injector and cartridge a kind of interlock is provided which impedes and prevents establishing of a fluid transferring coupling of cartridge and injector outside the drug delivery device. It is particularly due to such an interlock, that cartridge and injector can be preassembled to form the disposable delivery assembly and that the delivery assembly could be commercially distributed to end consumers and patients. Moreover, by the interlock formed by the at least one stop member and the correspondingly-shaped stop face a mutual fluid transferring coupling of injector and disposable cartridge can be established directly before a dispensing action takes place.

According to another embodiment one of cartridge and injector comprises a linear guiding to engage with a guide section of the other one of cartridge and injector. By means of the linear guiding, a well-defined relative displacement of cartridge and injector can be provided by way of which injector and cartridge can be displaced relative to each other between the undeployed configuration and the deployed configuration. Typically, the linear guiding serves to linearly or translationally displace the cartridge relative to the injector when transferring cartridge and injector from the undeployed configuration to the deployed configuration. The linear guiding may also serve to interconnect cartridge and injector in both, the undeployed configuration as well as in the deployed configuration.

Mutual displacement of cartridge and injector along the linear guiding may be limited at least in one direction, namely towards the deployed configuration. Mutual displacement of cartridge and injector may also be limited in an opposite direction, hence towards the undeployed configuration in order to keep disposable cartridge and disposable connector unreleasably together in order to avoid disassembly of the disposable delivery assembly. In this way separation of injector and cartridge can be avoided and a potential misuse, e.g. in form of coupling a new cartridge with a used injector can be effectively impeded.

According to a further embodiment, the injector fluid coupling comprises a cannula extending parallel to the linear guiding and which cannula is adapted to penetrate a cartridge fluid coupling's pierceable seal. The cannula of the injector fluid coupling is typically in permanent fluid communication with the disposable injector's flexible tube. The pierced cannula is particularly adapted to pierce and to penetrate the cartridge fluid coupling's seal so as to enter the interior of the cartridge and to provide access to the liquid medicament contained therein.

Since the cannula extends substantially parallel to the linear guiding, mutual displacement of the cartridge relative to the injector automatically leads to the penetration of the cartridge fluid coupling's pierceable seal by the pierced cannula. The linear guiding typically provides and defines the direction of mutual displacement of cartridge and injector. In this way, the linear guiding also provides retraction of the cannula from the fluid coupling's pierceable seal. In the undeployed configuration, the cannula, hence its pointed tip is located at a well-defined distance from the cartridge's pierceable seal. It is only upon the displacement of the cartridge relative to the injector into the deployed configuration in which the cannula enters and penetrates the pierceable seal.

According to another aspect a drug delivery device for dispensing of a liquid medicament is provided. The drug delivery device, typically implemented as a peristaltic pump comprises a housing having at least one feeder member, typically in form of a rotatable pump head. Moreover, the drug delivery device comprises a receptacle to receive the undeployed delivery assembly as described above. In addition, the drug delivery device also comprises a fastener to releasably fix the delivery assembly in or at the receptacle.

In particular, the receptacle of the drug delivery device is adapted for insertion of the disposable delivery assembly only when in undeployed configuration. In the event that the disposable delivery assembly would be deployed prior to assembly into the receptacle, insertion of the delivery assembly into the receptacle is typically prevented or its fixing to the drug delivery device by means of the fastener is impeded or is simply not possible. In this way, the mutual interaction of the drug delivery device's receptacle with the disposable delivery assembly requires and enforces exclusive insertion of an undeployed delivery assembly which is to be deployed only when located in the receptacle prior to an initial delivery- or dispensing action.

According to a further embodiment the fastener of the drug delivery device is operably engageable with at least one of the cartridge and injector. The fastener is particularly configurable from a release configuration into a locking configuration to mutually displace cartridge and injector into the deployed configuration. Typically, when inserting the undeployed delivery assembly into the drug delivery device's receptacle the fastener is in a release configuration. Due to its interaction with at least one of injector and cartridge it is the fastener that transfers the disposable delivery assembly from the undeployed configuration into the deployed configuration by transferring the fastener from the release configuration into the locking configuration.

Typically, transfer of the fastener between release configuration and locking configuration comes along with a displacement of at least a portion of the fastener parallel to the linear guiding of the disposable delivery assembly. Moreover, the fastener is typically engageable with only one of cartridge and injector in regard of a displacement along the linear guiding while the other one of cartridge and injector is fixed to the housing. In this way, transferring of the fastener from the release configuration into the locking configuration induces a respective displacement of the disposable cartridge relative to the disposable injector, thereby establishing a fluid transferring interconnection of cartridge and injector.

According to another embodiment the fastener is pivotally connected to the housing between an opened configuration and a closed configuration. The receptacle is accessible only in the opened configuration of the fastener. In closed configuration of the fastener the receptacle is at least partially covered by the fastener. In this way, the fastener belonging to the housing of the drug delivery device may effectively serve as a lid to open and to close a receptacle for the disposable delivery assembly.

In a closed configuration the fastener may also cover the delivery assembly located in the receptacle. In this way, the delivery assembly may not be discernible or recognizable outside the drug delivery device.

According to a further embodiment the fastener comprises a base portion pivot mounted to the housing. The base portion comprises a rear panel extending radially from a pivot axis into the receptacle upon pivoting the fastener from the closed configuration towards the opened configuration. In the closed configuration the rear panel may extend substantially parallel and adjacent to a rear wall of the receptacle. By way of pivoting the fastener and hence its base portion from the closed configuration towards the open configuration the rear panel, in particular a free end thereof extends into the receptacle. It may then abut and engage with at least one of injector and cartridge of the disposable delivery assembly in order to return the delivery assembly from the deployed configuration into the undeployed configuration.

It is of particular benefit that the disposable delivery assembly reaches the undeployed configuration when the fastener reaches the open configuration in which the receptacle of the drug delivery device is accessible to remove the disposable delivery assembly therefrom. By means of the rear panel of the fastener's base portion the fluid transferring coupling of cartridge and injector can be abrogated so that the disposable delivery assembly can be removed from the drug delivery device's receptacle in the undeployed configuration in which the injection needle of the disposable injector is no longer in fluid communication with the cartridge. In this way, droplet generation at a distal end of the injection needle and hence contamination of the environment by the medicament can be effectively impeded and avoided.

According to another embodiment the fastener also comprises a decoupler which is configured to engage with at least one of the stop member and the stop face of injector and cartridge when the fastener reaches the closed configuration. By means of the decoupler, the mutual abutment and engagement of injector's and cartridge's stop member and stop face can be at least temporally suspended. When reaching the closed configuration the fastener effectively suspends the interlock of cartridge and injector thereby allowing to displace cartridge and injector along the linear guiding to reach the deployed configuration. In an alternative, it is also conceivable, that the decoupler just becomes active to suspend the interlock configuration of injector and cartridge when initially transferring the fastener from the release configuration into the locking configuration.

In any case, the well-defined interaction of the decoupler with at least one of stop member and stop face of cartridge and injector enables mutual displacement of injector and cartridge along the linear guiding only when the fastener is in closed configuration.

According to another embodiment the receptacle of the drug delivery device comprises a recessed structure to engage with an injector's complementary-shaped mating structure. In this way, the injector can be fixed in the receptacle in regard to a deploy direction. Typically, the fastener is configurable between the release configuration and the locking configuration by displacing a portion thereof along the deploy direction. The displacement of the fastener's portion along the deploy direction is directly transferable to and into a respective displacement of the cartridge along the deploy direction. By fixing the injector in the drug delivery device's receptacle in regard of the deploy direction, e.g. by means of the receptacle's recessed or protruding structure engaging with the complimentary-shaped mating structure of the injector, the injector is effectively fixed in the receptacle so that a displacement in deploy direction induced by the fastener exclusively acts on the cartridge, thereby displacing the cartridge in deploy direction relative to the injector. In typical embodiments, the deploy direction along which a portion of the fastener is displaceable to either reach the release configuration or the locking configuration is substantially parallel to the linear guiding of injector and cartridge when the fastener is in closed configuration.

In another embodiment the fastener comprises a slider. By means of the slider the fastener is transferable from the release configuration into the locking configuration. Typically, the slider is displaceably attached to the base portion of the fastener. The slider may form a free end of the fastener and may be radially displaceable relative to the base portion in regard of a pivot axis by way of which the base portion and hence the fastener is pivotably connected to the drug delivery device's housing. By means of the slider, the radial extension of the fastener in regard to the pivot axis can be modified between an extended position, typically corresponding to the release configuration and a retracted position, typically corresponding to the locking configuration. It is particularly intended that the fastener is transferable between the release and the locking configuration when in closed configuration. By means of the slider a linear displacement and hence a linear extension and retraction of a portion of the fastener can be provided to induce a correspondingly directed linear displacement of the cartridge relative to the injector.

In another embodiment the fastener comprises a pivotable lid with a free end formed by the slider. In closed configuration of the fastener the slider at least partially encloses the cartridge. In this configuration it is retractable from the extended position into the retracted position along the deploy direction, thereby displacing the cartridge relative to the injector into the deployed configuration. Typically, the slider comprises a front face, hence an inside-facing sidewall portion of a front face that directly engages and abuts with a correspondingly-shaped outside facing front face of the cartridge. When in closed configuration and by displacing the slider in the deploy direction, the respective displacement is unalterably transferable to the cartridge towards the deploy configuration and hence along the linear guiding so that the injector fluid coupling's cannula pierces and penetrates the cartridge fluid coupling's pierceable seal.

In a further embodiment the slider comprises a latch member to releasably engage with a housing's corresponding latch member when displacing the slider into at least one of retracted position and extended position. Typically, the slider's latch member only engages with a housing's corresponding latch member when reaching the retracted position when the fastener is in closed configuration. In this way, the slider serves as a lock or interlock for keeping the fastener in the closed configuration relative to the housing. In addition, by way of mutually corresponding latch members of slider and housing also the slider and hence the fastener may be kept in the locking configuration.

By means of the mutually corresponding latch members of slider and housing, the fastener can be interlocked to the housing in order to keep the housing's receptacle closed and to prevent self-acting disassembly or removal of the disposable delivery assembly from the drug delivery device. Typically, mutually corresponding latch members of the slider and the housing may engage and disengage along the deploy direction. By displacing the slider from the extended position into the retracted position, by way of which the disposable delivery assembly is also transferred from the undeployed into the deployed configuration, the mutually corresponding latch members of slider and housing engage, thereby keeping the fastener in the closed configuration, in which the disposable delivery assembly is securely fixed to the drug delivery device, in particular in the receptacle thereof.

According to another embodiment the rear panel of the fastener engages with the cartridge to displace the cartridge relative to the injector towards and into the undeployed configuration when pivoting the fastener from the closed configuration into the opened configuration. While pivoting the fastener from the open configuration into the closed configuration is substantially effectless in regard of the initial undeployed configuration of disposable injector and disposable cartridge the rear panel of the fastener is exclusively operable for displacing cartridge and injector into the undeployed configuration in the course of removing and replacing the disposable delivery assembly.

Accordingly and following another embodiment transferring of the fastener from the open configuration into the closed configuration is blocked by the fastener's rear panel colliding with a deployed delivery assembly located in the receptacle. The rear panel of the fastener is of particular relevance during a closing operation of the fastener. When in undeployed configuration cartridge and injector are positioned in such a way that they provide room for the rear panel of the fastener to enter the drug delivery device's receptacle during a closing operation of the fastener. In the event that for some reason injector and cartridge should be assembled in the receptacle when in deployed configuration the outer contour or structure of one of injector and cartridge collides with the rear panel thereby preventing that the fastener reaches the closed configuration.

In this way, the mutual interaction of the rear panel with the disposable delivery assembly prevents closing of the fastener when the disposable delivery assembly is assembled in the drug delivery device's cartridge in a deployed configuration. The fastener and its rear panel as well as the contour and geometries of the cartridge and/or the injector are adapted such, that a collisionless closing of the fastener from the opened configuration into the closed configuration is only possible and allowed when the delivery assembly is in undeployed configuration. In this way, patient safety and patient compliance can be further improved.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser- Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the art that various modifications and variations can be made to the present invention without departing from the spirit and scope of the invention. Further, it is to be noted, that any reference numerals used in the appended claims are not to be construed as limiting the scope of the invention.

BRIEF DESCRIPTION OF THE DRAWINGS

In the following an embodiment of the disposable delivery assembly in connection with a drug delivery device is described in more detail by making reference to the drawings, in which:

FIG. 10 shows the cartridge in an isolated perspective view, FIG. 11 shows the cartridge according to FIG. 10 in an exploded view, FIG. 12 shows the cartridge in longitudinal cross-section, FIG. 13 shows a side view of disassembled disposable injector and disposable cartridge, FIG. 14a shows the disposable delivery assembly in undeployed configuration, FIG. 14b shows the delivery assembly during a release of the interlock of stop member and stop face, FIG. 14c shows the disposable delivery assembly in a deployed configuration, FIG. 15a shows a cross-section through the delivery assembly according to FIG. 14a and FIG. 15b shows the disposable delivery assembly in cross-section in the deployed configuration according to FIG. 14c.

DETAILED DESCRIPTION

Figure 1:
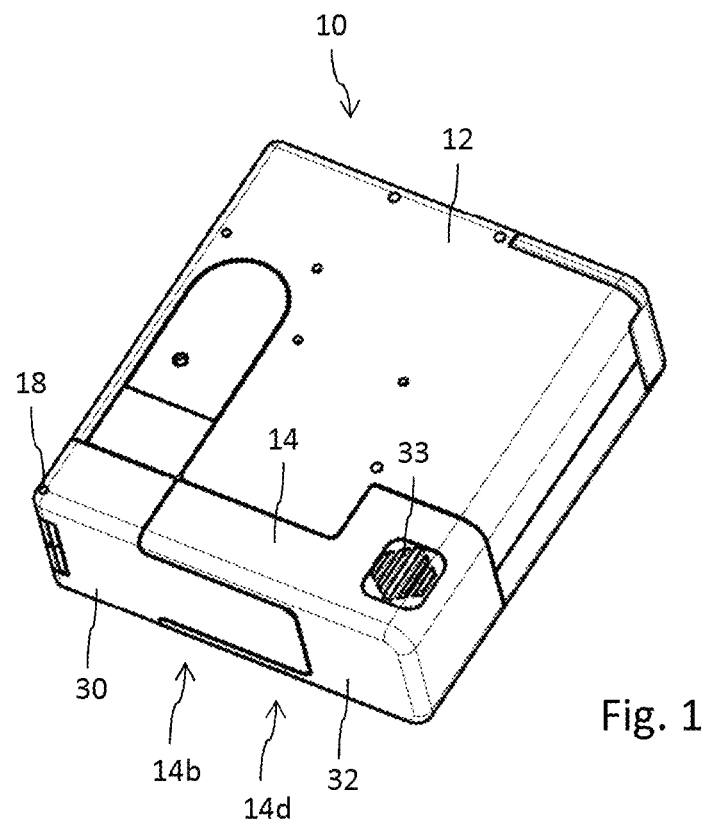
FIG. 1 schematically shows the drug delivery device in a perspective view with the fastener in closed and retracted position.
Figure 2:
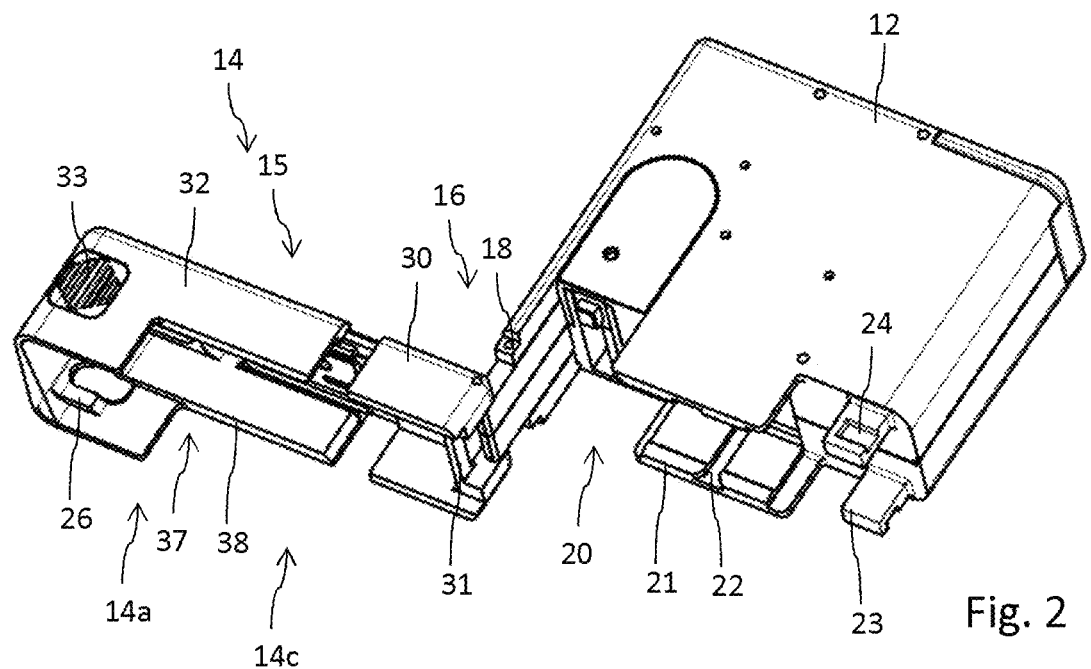
FIG. 2 shows the drug delivery device with the fastener in opened and extended configuration.
Figure 3:
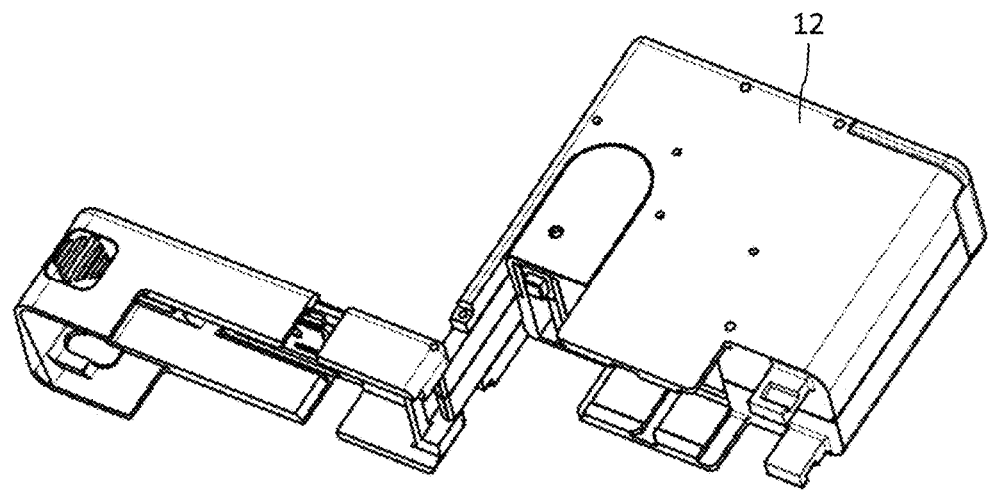
FIG. 3 shows the disposable delivery assembly during insertion into the receptacle of the drug delivery device.
Figure 4:
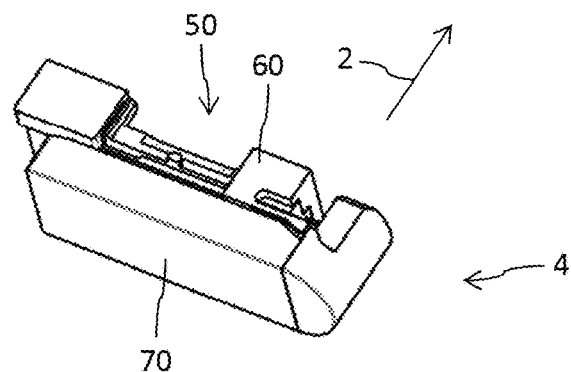
FIG. 4 shows a perspective view of the drug delivery device with the disposable delivery assembly assembled thereto.
Figure 4:
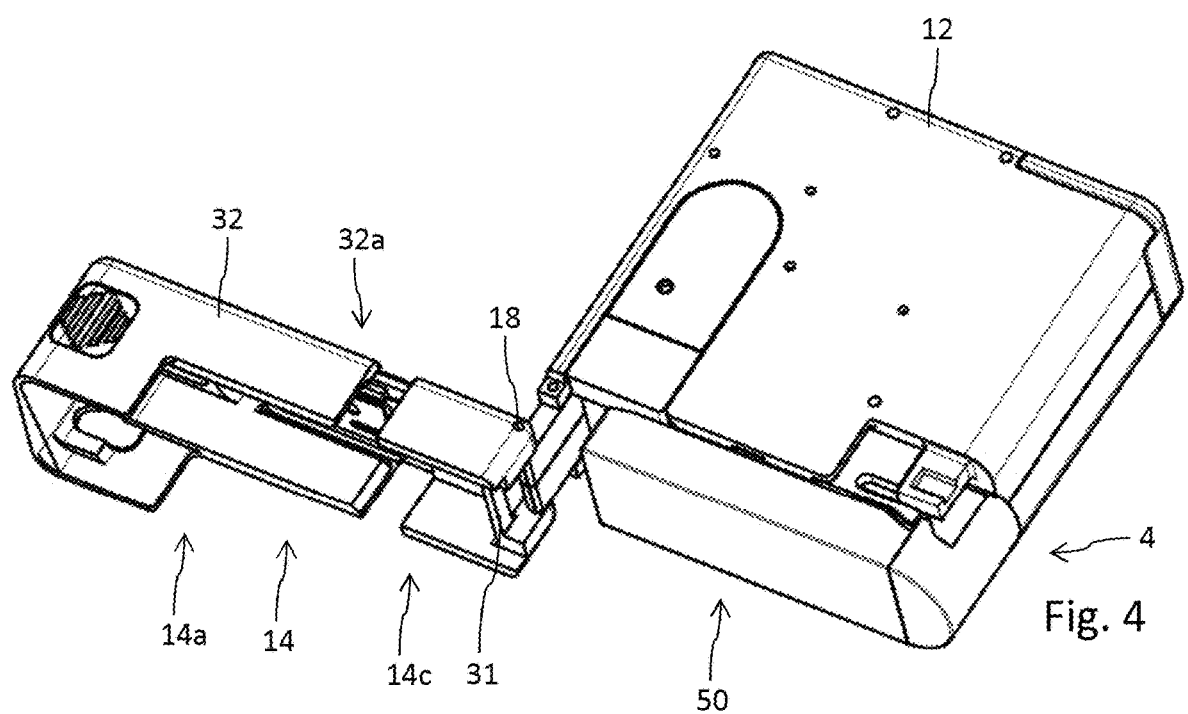
Figure 5:
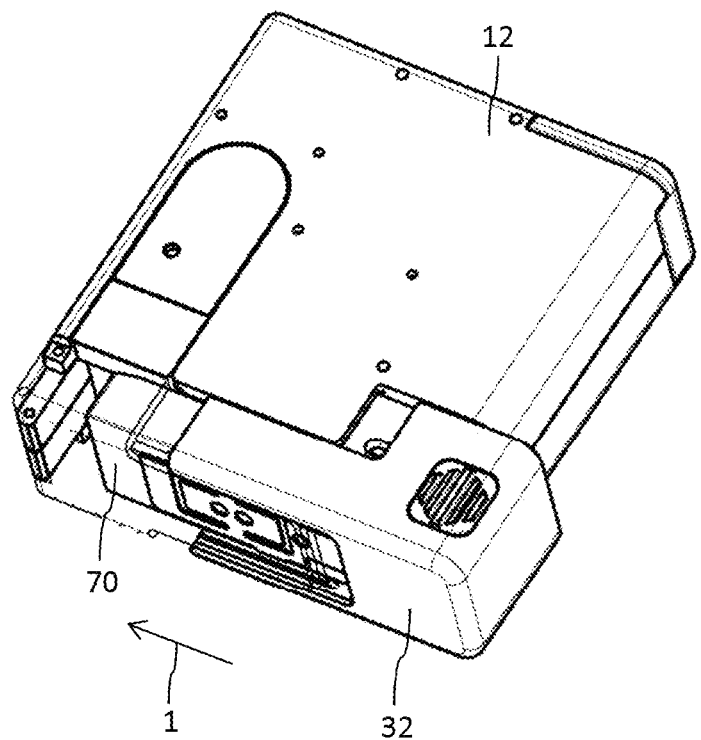
FIG. 5 shows the drug delivery device with the fastener in closed but extended configuration.

The drug delivery device 10 as it is illustrated in FIGS. 1-5 comprises a housing 12 featuring a receptacle 20 which is closeable by a fastener 14 that serves as a lid 15 for the receptacle 20. The fastener 14 is pivot mounted to the housing 12 by means of a hinge 16. Consequently, the fastener 14 is pivotable between a closed configuration 14d as shown in FIGS. 1 and 5 and an opened configuration 14c as illustrated in FIGS. 2-4. In the opened configuration 14c, the receptacle 20 is accessible from outside to insert a disposable delivery assembly 50 as for instance illustrated in FIG. 3. The delivery assembly 50 is insertable into the receptacle 20 along an insert direction 2 as illustrated in FIG. 3.

Figure 7:
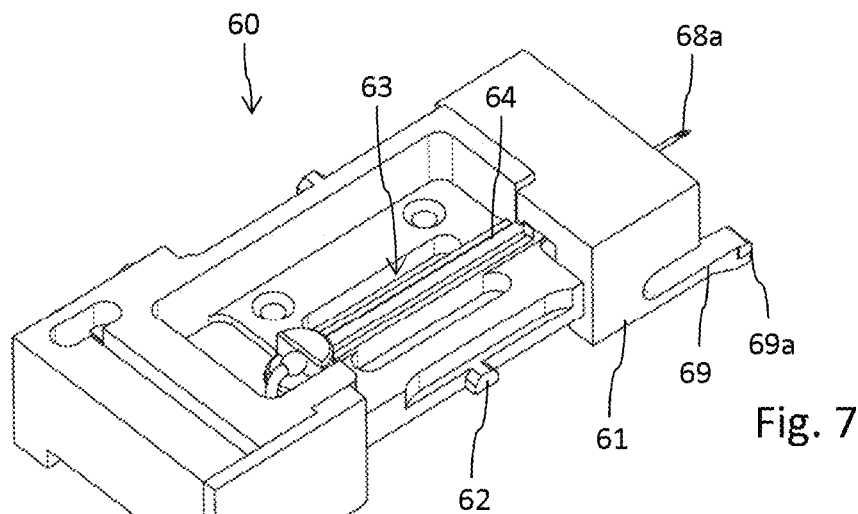
FIG. 7 shows the disposable injector in a perspective view.
Figure 8:
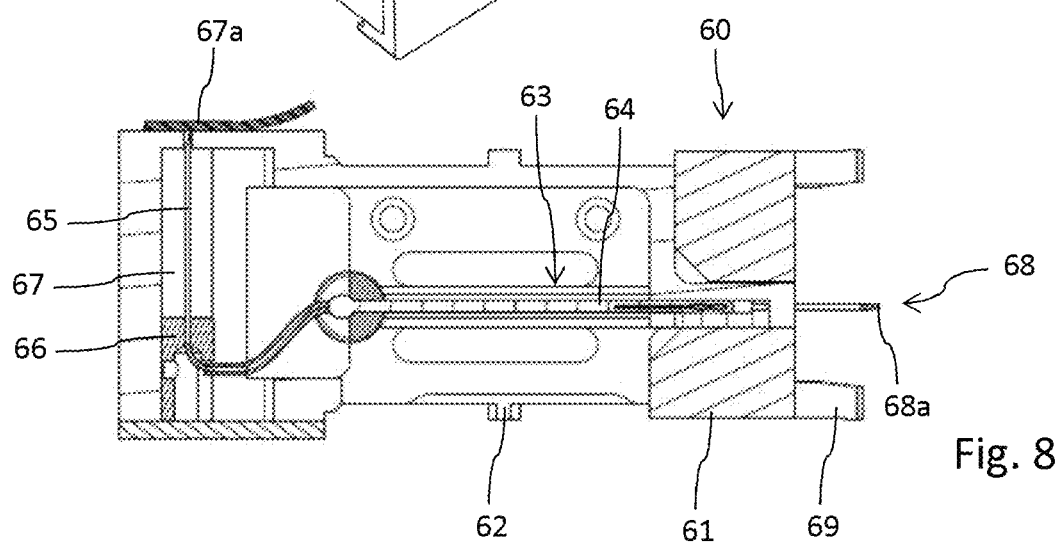
FIG. 8 shows a cross-section through the disposable injector in an initial configuration and FIG. 9 shows the injector according to FIG. 8 with an extended injection needle.
Figure 9:
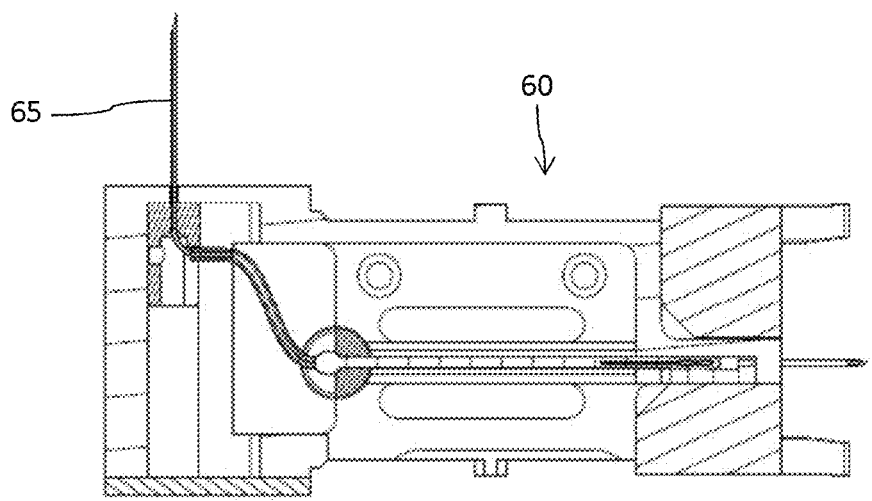

The disposable delivery assembly 50 comprises a disposable injector 60 as illustrated in FIGS. 7-9 and further comprises a disposable cartridge 70 as shown in FIGS. 10-12. Disposable injector 60 and disposable cartridge 70 are mechanically interconnected in an undeployed configuration 4 as for instance shown in FIGS. 14a and 15a. In this configuration disposable injector 60 and disposable cartridge 70 are mechanically engaged and connected but are not yet in fluid communication. A fluid communication is yet to be established upon transferring the fastener 14 from a release configuration 14a as shown in FIG. 5 into a locking configuration 14b as shown in FIG. 1.

The disposable injector as shown in FIG. 7 comprises a base 61. The base features a track 63 through which a flexible tube 64 is guided. In the region of the track 63 the feeder member 100 or the pump head of the drug delivery device 10 engages with the flexible tube 64. Here, the flexible tube 64 is squeezed by the feeder member 100 in order to transport the liquid medicament from the reservoir 80 of the cartridge 70 towards an injection needle 65 of the injector 60. The injection needle 65 is also a component of the injector 60. As can be seen from a comparison of FIGS. 8 and 9, the injection needle 65 is attached to a piston 66, which is slideably received in a conduct 67. An outlet of the conduct 67 is covered by a protector 67a as shown in FIG. 8. Upon activation of the injector 60 the protector 67a typically in form of an adhesive foil is to be removed, hence allowing the piston 66 to slide along the conduct 67 thereby advancing the injection needle 65 into an extended position as illustrated in FIG. 9.

Typically, when arranged in the receptacle 20 of the drug delivery device 10 that side face of the injector 60 featuring the outlet for the injection needle 65 forms an integral component of the outer surface or housing 12 of the drug delivery device 10. In typical application scenarios, the drug delivery device 10 is e.g. adhesively attached to the skin of a patient. Upon activation of the injector 60, hence upon activation of the drug delivery device 10 the injection needle 65 is automatically positioned into the extended position thereby piercing or penetrating dermal tissue for transdermal or subcutaneous injection of the liquid medicament.

Opposite the injection needle 65 the injector 60 comprises an injector fluid coupling 68, presently in form of a hollow but tipped cannula 68a. As becomes apparent from FIGS. 8 and 9, the injector fluid coupling 68 extends from a sidewall of the injector's base 61. The tipped injector fluid coupling 68 serves to penetrate and to pierce a cartridge fluid coupling 90 as for instance illustrated in FIG. 12. The cartridge fluid coupling 90 comprises a pierceable seal 82, typically in form of a sealing disc. The pierceable seal 82 closes a fluid channel 86 which is in fluid communication with the interior of a reservoir 80 containing the liquid medicament. The reservoir 80 comprises a flexible bag 81 which allows and supports a suction-based withdrawal of a medicament therefrom. The outlet of the fluid channel 86 is closed by the pierceable seal 82, which is secured within an opening of a base of the cartridge 70 by means of an insert 84. The insert 84 comprises a central through opening 85 which allows to receive the tipped injector fluid coupling 68, hence the cannula 68a. The pierceable seal 82 typically serves as a septum of elastic material, which may even be pierced multiple times without exhibiting substantial leakage.

The cartridge 70 features a base 74 having and forming a fluid channel 86 and further has a housing 71 providing a protective sheath for the flexible bag 81 forming the reservoir 80 for the liquid medicament.

The base 74 further comprises a socket 76 extending from a planar surface of the base 74. The socket 76 extends into the flexible bag 81 so as to close an opening of the flexible bag. In addition and in order to seal the interconnection of flexible bag 81 and the socket 76, the socket comprises an annular or surrounding groove 78 at its outer circumference. In addition and as becomes apparent from FIG. 12, the housing 71 features a receptacle to engage with the socket 76 in a press fit. Here, the housing 71 extends over and all around the socket 76 and an O-ring 77 located in the socket's groove 78, thereby squeezing and fixing the flexible bag 81 therebetween.

In this way, a sealed interconnection of socket 76 and flexible bag 81 can be provided without any adhesives and without application of thermal energy. By having a press fit arrangement of the flexible bag 81 with the socket 76 a rather medicament friendly seal can be provided.

The fluid channel 86 extends from a middle portion of the socket's 76 front face 75 into the base 74. As shown in FIG. 12, the fluid channel 86 extends substantially horizontal and then vertically upwardly before it merges and extends into an outlet section that is sealed by the pierceable seal 82. The outlet section forming the cartridge fluid coupling 90 is arranged and oriented substantially parallel to the lower portion of the fluid channel 86 which is in extension of the reservoir 80 and parallel to a linear guiding 72 as will be explained below. In this way, the pierceable seal 82 can be pierced and penetrated by the injector fluid coupling 68, hence by its cannula 68a. At an upper portion of the vertical segment of the fluid channel 86 there is located a closure 88 that may serve as a ventilation. The closure 88 may be removable to eventually refill the reservoir 80 by a refill- or retail service. The insert 84 that keeps the pierceable seal 82 in position may comprise an outer thread to engage with an inner thread of a corresponding opening of the base 74. Alternatively, the insert 84 is press fitted or squeezed in the base 74.

As it is further illustrated in FIG. 11 the front face 75 of the socket 76 comprises several grooves 79 that extend across the front face 75 towards the outer circumference or to the outer edge thereof. All these grooves 79 merge with the central fluid channel 86. Since the flexible bag 81 is of flexible material it is conceivable that a portion thereof may get in abutment with a portion of the front face 75 when extracting the liquid medicament from the reservoir 80. Here, the grooves 79 provide a respectable fluid flow even in case that the portion of the front face 75 coinciding with the fluid channel 86 should be obstructed or should get in abutment with an inside-facing portion of the flexible bag 81.

Figure 6:
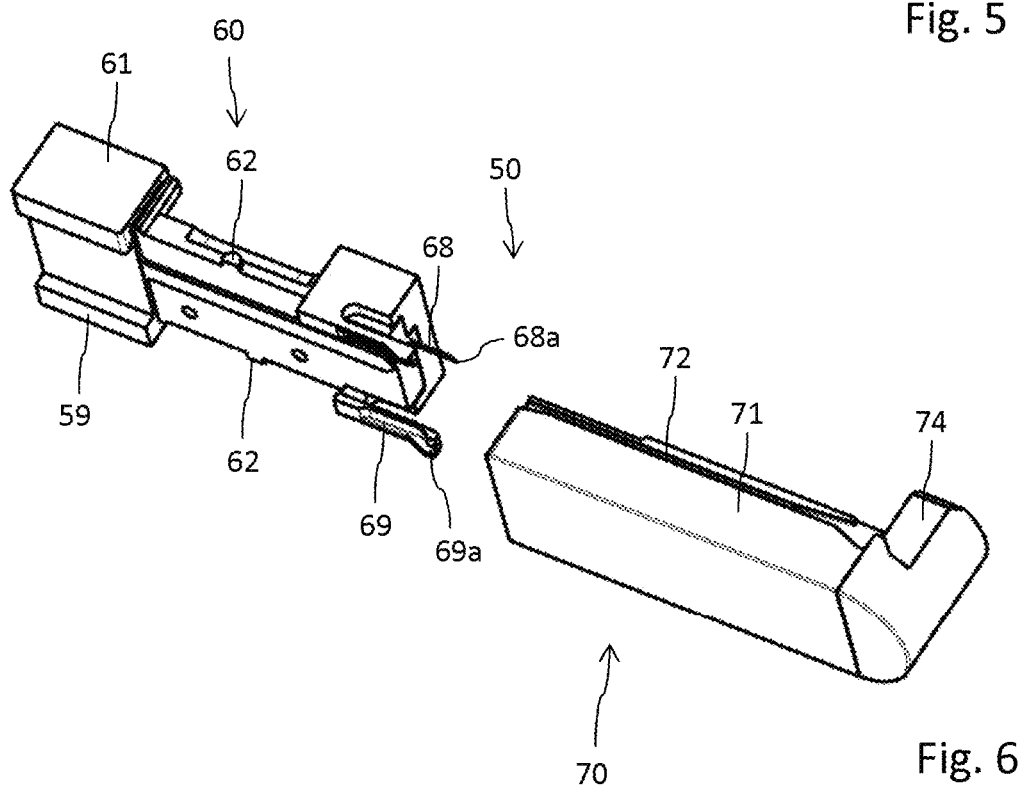
FIG. 6 is an isolated perspective and exploded view of the disposable delivery assembly with disassembled disposable injector and disposable cartridge.

The housing 71 of the cartridge 70 further comprises a linear guiding 72, e.g. in form of a longitudinal groove as illustrated for instance in FIG. 10. The linear guiding 72 cooperates and engages with a guide section 59 of the injector as illustrated in FIG. 6. In this way, cartridge 70 and injector 60 can be mechanically connected in a well-defined way but undeployed configuration, in which the cannula 68a of the injector 60 does not yet penetrate or pierce the pierceable seal 82 of the cartridge 70. The linear guiding 72 further supports and defines a mutual linear and straight displacement of the disposable injector 60 relative to the cartridge 70. Hence, the cartridge 70 may be displaced along the linear guiding 72 with regard to the injector 60 being fixed in the housing 20.

In an initial and undeployed configuration 4 as illustrated in FIG. 14a, the injector 60 and the cartridge 70 are mutually assembled in such a way, that the stop member 69 protruding from a sidewall portion of the injector 60 is in abutment with a corresponding stop face 73a of the cartridge 70. The linear guiding 72 provided as a linearly and rather straight extending groove at a sidewall portion of the housing 71 features a recess 73 formed by a beveled portion of the linear guiding. As shown for instance in FIG. 14a, the stop member 69 of the injector 60 comprises a shape that corresponds to the beveled recess 73.

Consequently, when reaching the undeployed configuration 4 as shown in FIG. 14a, the flexible deformable stop member 69 enters the beveled recess 73 of the linear guiding 72 and abuts with the vertically-extending stop face 73a of the cartridge 70. In this way, any further displacement of the disposable cartridge 70 towards the left hand side, hence towards the disposable injector 60 is impeded and prevented. It is only upon interaction with a decoupler 37 of the drug delivery device's 10 fastener 14 that the interlock between injector 60 and cartridge 70 can be abrogated or suspended.

Figure 16:
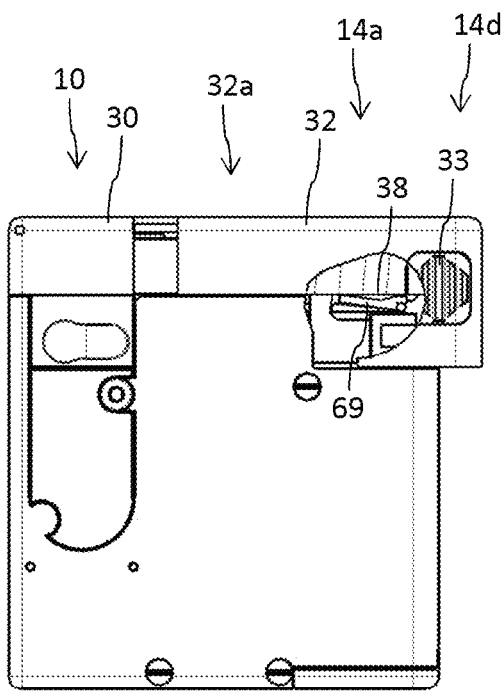
FIG. 16 shows a partial cross-section of the drug delivery device with the fastener in closed but extended configuration.

The decoupler 37 may be simply provided by or integrated into a sidewall portion 38 of the lid-shaped fastener 14. As illustrated in FIG. 16 and when reaching a closed configuration 14d the pivotable or flexible deformable stop member 69 is pressed downwards so to leave the recess 73 of the cartridge 70, thereby allowing that the cartridge 70 can be further displaced towards the deploy direction 1 until it reaches the deployed configuration 6 as illustrated in FIG. 14c.

Comparing of FIGS. 15a and 15b, each of which illustrating the disposable delivery assembly 50 in undeployed configuration 4 and in deployed configuration 6, respectively, reveals that only in the deployed configuration 6 the cannula 68a penetrates the pierceable seal 82 of the cartridge thereby providing and establishing a fluid communication between the reservoir 80 and the injection needle 65.

Due to the interaction of the stop member 69 with the correspondingly-shaped stop face 73a a premature fluid transferring coupling of injector 60 and cartridge 70 can be effectively prevented. When commercially distributed by a manufacturer, disposable injector 60 and disposable cartridge 70 may be provided as a preassembled disposable delivery assembly 50 as shown in FIGS. 3 and 14a. Deployment of injector and cartridge, hence establishing of a fluid transferring interconnection of injector 60 and cartridge 70 may only take place through interaction with the fastener 14 of the drug delivery device 10.

In the same way also a disconnecting and decoupling of disposable cartridge 70 and disposable injector 60 after consumption of the medicament the interaction with the fastener 14 upon opening the receptacle 20 may provide a self-acting and automated disconnection of cartridge 70 and injector 60. Contamination of the environment by droplets of the medicament rinsing out of the injection needle 65 can therefore be effectively avoided. Also here it is conceivable that cartridge 70 and injector 60 comprises mutually corresponding tamper proof members, which serve to avoid reconnection or redeployment of cartridge 70 and injector 60 once they have been transferred from the deployed configuration 6 back into the undeployed configuration 4.

Figure 17:
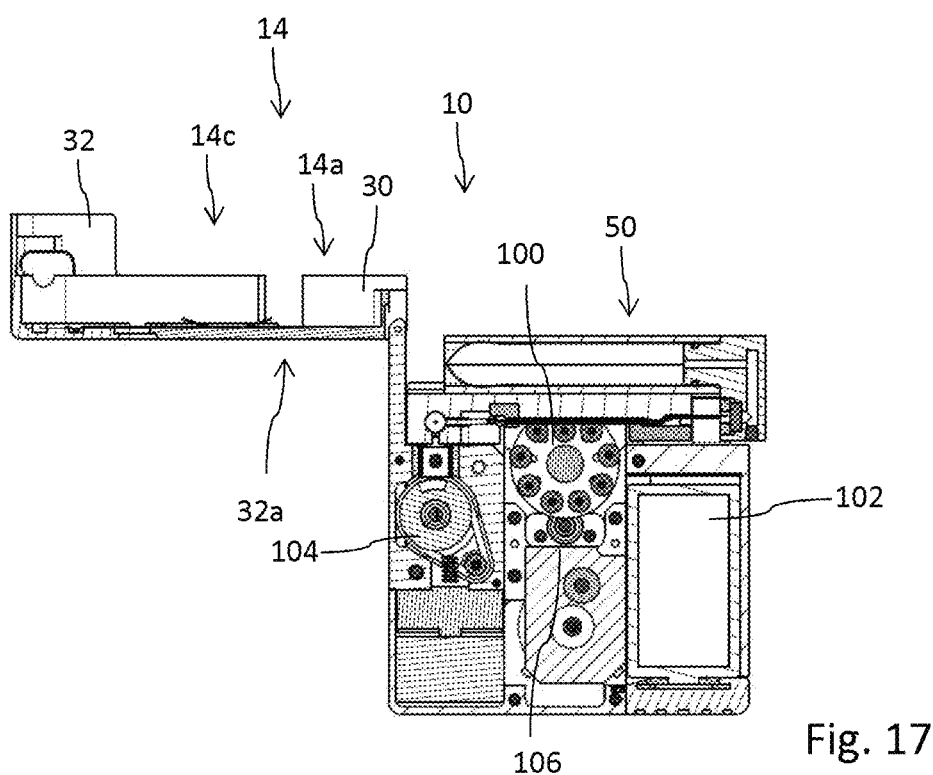
FIG. 17 is a cross-section through the drug delivery device.
Figure 18:
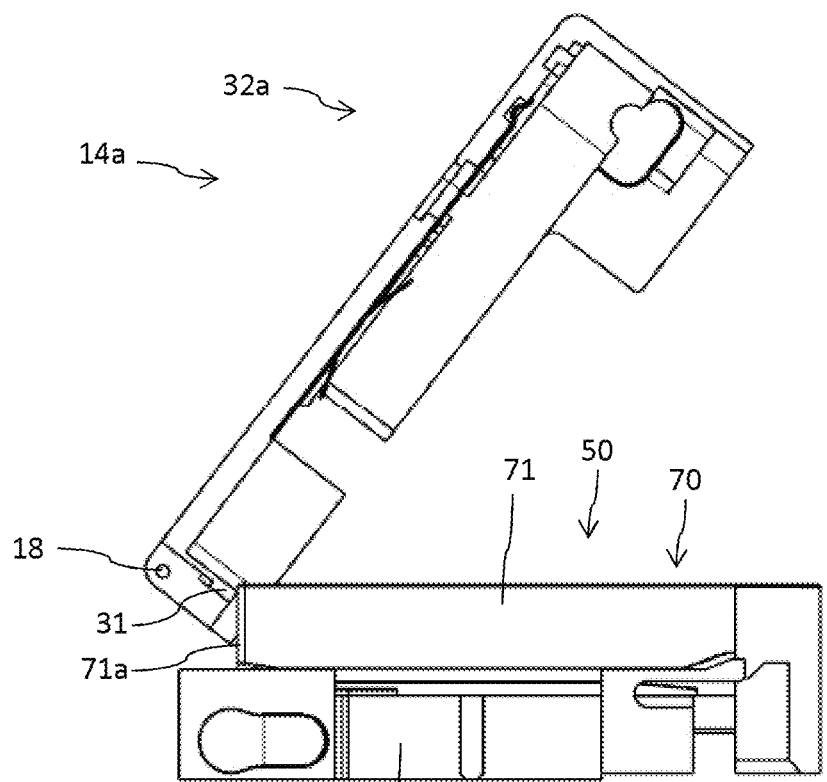
FIG. 18 shows an isolated side view of the interaction between the fastener's rear panel and the cartridge during an opening movement.

The drug delivery device 10 as for instance illustrated in FIG. 17 is designed and implemented as a peristaltic pump. It comprises a feeder member 100, presently in form of a rotatable pump head that engages with the flexible tube 64 in order to squeeze the same for drug delivery. In addition, the drug delivery device 10 comprises an energy source, typically in form of an electric battery 102. Moreover, it comprises an injection drive 104 by way of which the injection needle 65 can be displaced along the conduct 67. By means of the injection drive 104 the injection needle 65 can be displaced from an initial position into an extended position as shown in FIG. 9. In the same way the injection drive 104 may serve to retract the extended injection needle 65. Additionally, the peristaltic pump 10 comprises a delivery drive 106 in order to set the pump head, hence the feeder member 100 in rotation during and for drug delivery.

In the present embodiment the complete disposable delivery assembly 50 is insertable along an insert direction 2 into the opened receptacle 20 as indicated in FIG. 3. The sidewall 21 of the receptacle 20, which belongs to the housing 12 of the drug delivery device 10 comprises a recessed structure 22, e.g. in form of a groove extending parallel to the insert direction 2. It is the injector 60 that comprises a correspondingly-shaped mating structure 62 as for instance shown in FIGS. 7 and 8. By inserting the injector 60 with the outwardly-extending protrusion 62 into the grooves 22 of the receptacle 20, only the disposable injector 60 of the delivery assembly 50 can be secured and fixed to the housing 12 of the drug delivery device 10 in regard to the deploy direction 1, which in the present embodiment extends substantially perpendicular to the insert direction 2.

In the undeployed configuration 4 as for instance shown in FIGS. 3 and 4 the base 74 of the cartridge 70 at least partially extends beyond the outer circumference of the adjacently-located housing portion of the drug delivery device 10. In the undeployed configuration 4 as shown in FIG. 4, the fastener 14 is pivotable from the opened configuration 14c as shown in FIG. 4 into the closed configuration 14d as shown in FIG. 5. The pivotable fastener 14 comprises two portions, namely a base portion 30 by way of which the fastener 14 is pivotably attached to the housing 12 via a hinge 16. Attached to the base portion 30 the fastener 14 comprises a slider 32 forming a free end of the fastener 14 effectively providing a lid 15.

Figure 19:
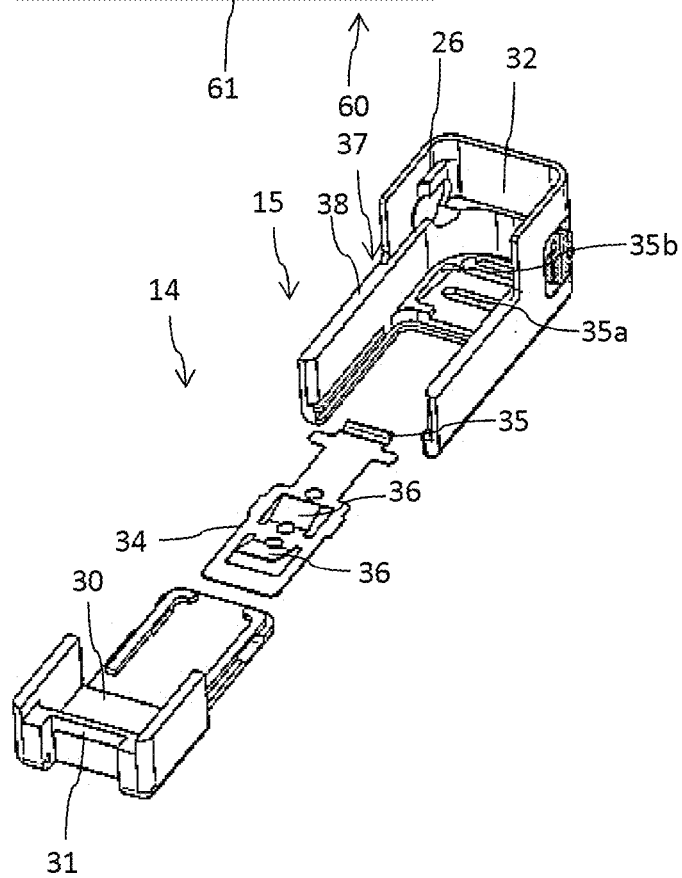
FIG. 19 shows an exploded view of the various components of the fastener.
Figure 20:
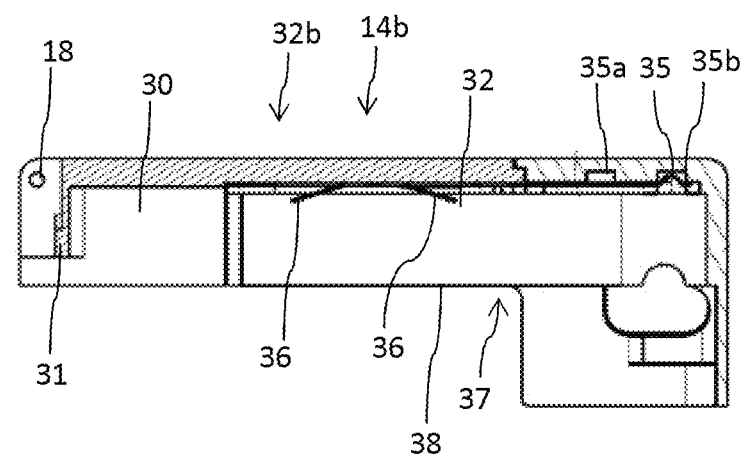
FIG. 20 shows a cross-section through the fastener in retracted configuration and FIG. 21 shows the fastener in the extended, hence in the release configuration.
Figure 21:
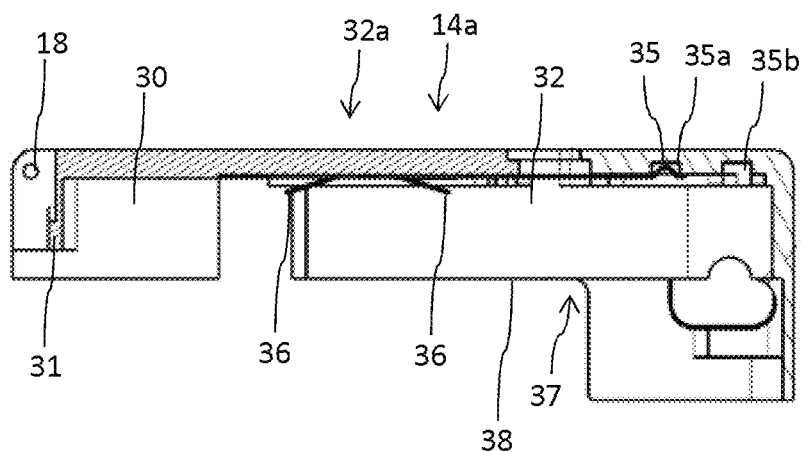

The slider 32 and the base portion are interconnected by means of a planar spring 34 as shown in FIG. 19. The spring 34 comprises a latch portion 35 to engage with two recesses 35a, 35b at an inside-facing portion of the slider 32. By way of the latch portion 35 engaging with either a distal recess 35b or with a proximal recess 35a, as indicated in FIGS. 20 and 21 the radial position of the slider 32 with regard to the base portion 30 and in regard to the hinge 16 and the pivot axis 18 can be modified. By means of the spring 34 and its latch portion 35 the slider 32 can be transferred from an extended configuration as shown in FIG. 21 into a retracted position 32b as shown in FIG. 20.

By way of the mutual interaction of the latch portion 35 with one of the recesses 35a, 35b, the slider 32 can be interlocked either in the extended position 32a or in the retracted position 32b. In addition the spring 34 also comprises two wings 36 extending at an angle from the plane surface of the spring 34 and extending into the receptacle 20 when the fastener 14 is in its closed configuration 14d. The wings 36 provide a particular pressure onto the cartridge 70 to keep the cartridge well seated and fixed in the receptacle 20. The slider 32 forms a kind of a U-shaped receptacle for the cartridge 70, in particular for the cartridge's base 74. When in closed configuration 14d, an inside-facing sidewall portion 32 of the retracted slider 32 may directly abut with an outside-facing sidewall portion of the cartridge 70, in particular of its base 74. By closing the fastener, hence by transferring and pivoting the fastener 14 in the closed configuration 14d, in which the slider is in its extended position 32a, the fastener 14 is also in a release configuration 14a as shown in FIG. 5.

Now, by displacing the slider 32 into the retracted position 32b as shown in FIG. 1 the cartridge 70 is displaced relative to the injector 60 along the deploy direction 1 to establish a fluid communication between the cartridge fluid coupling 90 and the injector fluid coupling 68. Simultaneously and in the same way the slider 32, hence the free end portion of the fastener 14 directly engages with the housing 12 of the drug delivery device. As becomes apparent from FIG. 2, inside a sidewall portion of the slider's 32 free end there are located two horizontally extending latch members 26 that are adapted to engage with horizontally and correspondingly-shaped grooves 24 of a latch member 32 extending from the housing 12 of the drug delivery device.

The grooves 24 of the latch members 23 are open in a direction opposite the deploy direction 1. They are therefore suitable to receive the corresponding latch members 26 of the slider 32 when the slider 32 is displaced from the extended position 32a into the retracted position 32b along the deploy direction 1. The retracted position 32b of the fastener 14 effectively coincides with the locking configuration 14b, supposed that the slider 32 is displaced when the fastener 14 is in closed configuration 14d. Similarly, the extended position 32a of the slider 32 coincides with the release configuration 14a of the fastener 14 supposed that the fastener is in closed configuration 14d when the slider 32 is displaced relative to the base portion 30.

Once the medicament contained in the reservoir 80 has been withdrawn thus requiring a replacement of the cartridge 70 the slider 32 may be displaced in a direction opposite to the deploy direction 1, typically by means of the ripples 33 provided at the outer surface of the free end of the slider 32. As soon as the latch members 26, 24 of slider 32 and housing 12 disengage, the fastener 14 will be automatically lifted by a predefined portion due to the wings 36 of the spring 34 applying pressure to the upper surface of the cartridge 70. This is a clear indication to the user, that the drug delivery device 10 is in a maintenance mode. Now, by pivoting the fastener 14 from the closed configuration 14d into the opened configuration 14c, a rear panel 31 extending radially from the pivot axis 18 engages with a sidewall portion 71a of the housing 71 of the cartridge 70, thereby displacing the cartridge 70 along the linear guiding 72 relative to the injector 60 toward the undeployed configuration.

As a consequence, and when reaching e.g. a 90° opening configuration of the fastener 14, the injector 60 and the cartridge 70 are again in their undeployed configuration 4. Hence, the injector fluid coupling 68 is disconnected form the cartridge 70 and its reservoir 80 so that any eventual residual portions of the medicament left in the reservoir 80 may not leave the cartridge 70. Contamination of the environment through and by the medicament can therefore be reduced and prevented.

In addition, the rear panel 31 extending at least partially into the receptacle 20 is of particular benefit to provide an effective safeguard mechanism. When closing the fastener 14, hence when pivoting the fastener 14 from the opened configuration 14c into the closed configuration 14d it is required, that the rear panel 31 may freely enter a recessed portion between the cartridge 70 and the injector 60. In circumstances, wherein the disposable injector 60 and the disposable cartridge 70 should be arranged or inserted into the receptacle 20 already in a deployed configuration 6 closing of the fastener 14 is effectively prevented since the rear panel 31 would evidently collide with the cartridge 70, in particular with a housing 71 thereof that faces away from the base 74.

LIST OF REFERENCE NUMBERS 1 deploy direction
2 insert direction
4 undeployed configuration
6 deployed configuration
10 drug delivery device
12 housing
14 fastener
14a release configuration
14b locking configuration
14c opened configuration
14d closed configuration
15 lid
16 hinge
18 pivot axis
20 receptacle
21 sidewall
22 recessed structure
23 latch member
24 groove
26 latch member
30 base portion 31 rear panel
32 slider
32a extended position
32b retracted position
33 ripples
34 spring
35 latch portion
35a recess
35b recess
36 wing
37 decoupler
38 sidewall
50 delivery assembly
59 guide section
60 injector
61 base
62 mating structure
63 track
64 flexible tube
65 injection needle
66 piston
67 conduct
67a protector
68 injector fluid coupling
68a cannula
69 stop member
69a stop face
70 cartridge
71 housing
71a sidewall portion
72 linear guiding
73 recess
73a stop face
74 base
75 front face
76 socket
77 O-ring
78 groove
79 groove
80 reservoir
81 flexible bag
82 pierceable seal
84 insert
85 through opening
86 fluid channel
88 closure
90 cartridge fluid coupling
100 feeder member
102 battery
104 injection drive
106 delivery drive

The invention claimed is:

1. A disposable delivery assembly for a drug delivery device to dispense a liquid medicament, the disposable delivery assembly comprising:
a disposable injector comprising an injector base, an injection needle, a flexible tube, and an injector fluid coupling, wherein the injection needle is in fluid communication with the injector fluid coupling via the flexible tube, wherein the injector fluid coupling is fixed to the injector base; and
a disposable cartridge comprising a reservoir at least partially filled with the liquid medicament and comprising a cartridge fluid coupling in fluid communication with the reservoir,
wherein the disposable injector and the disposable cartridge are mechanically attached to each other in an undeployed configuration, in which the injector fluid coupling and the cartridge fluid coupling are disconnected, and
wherein the disposable cartridge is configured to be displaced relative to the injector base into a deployed configuration, in which the injector fluid coupling and the cartridge fluid coupling are in fluid communication,
wherein one of the disposable cartridge and the disposable injector comprises at least one stop member engaging with a correspondingly shaped stop face of the other one of the disposable cartridge and the disposable injector to impede self-acting displacement of the disposable cartridge and the disposable injector from the undeployed configuration into the deployed configuration, and
wherein a mutual abutment and engagement of the at least one stop member and the correspondingly shaped stop face is, at least temporarily, suspendable by a decoupler of a fastener of the drug delivery device.

2. The disposable delivery assembly according to claim 1, wherein the disposable cartridge and the disposable injector are pre-assembled by mechanically attaching the disposable cartridge to the injector base of the disposable injector, and wherein a pre-assembly of the disposable cartridge and the disposable injector is insertable into a receptacle of a housing of the drug delivery device only when the disposable injector and the disposable cartridge are in the undeployed configuration.

3. The disposable delivery assembly according to claim 1 consisting of the disposable cartridge and the disposable injector, and wherein the disposable injector and the disposable cartridge are directly mechanically connected when in the undeployed configuration.

4. The disposable delivery assembly according to claim 1, wherein the at least one stop member and the correspondingly shaped stop face provide an interlock operable to prevent transferring of the disposable cartridge and the disposable injector into the deployed configuration.

5. The disposable delivery assembly of claim 1, wherein the fastener is configured to releasably fix the disposable delivery assembly in or at a receptacle of the drug delivery device.

6. The disposable delivery assembly of claim 1, wherein the fastener is transferable from a release configuration into a locking configuration thereby inducing a displacement of the disposable cartridge relative to the injector base of the disposable injector into the deployed configuration.

7. The disposable delivery assembly according to claim 1, wherein one of the disposable cartridge and the disposable injector comprises a linear guiding configured to engage with a guide section of the other one of the disposable cartridge and the disposable injector.

8. The disposable delivery assembly according to claim 7, wherein the injector fluid coupling comprises a cannula extending parallel to the linear guiding and configured to penetrate a pierceable seal of the cartridge fluid coupling.

9. A drug delivery device for dispensing a liquid medicament, comprising:
a housing having at least one feeder member;
a receptacle to receive a disposable delivery assembly, the disposable delivery assembly comprising:
a disposable injector comprising an injection needle, a flexible tube, and an injector fluid coupling, wherein the injection needle is in fluid communication with the injector fluid coupling via the flexible tube, and a disposable cartridge comprising a reservoir at least partially filled with the liquid medicament and comprising a cartridge fluid coupling in fluid communication with the reservoir, wherein the disposable injector and the disposable cartridge are mechanically interconnected in an undeployed configuration, in which the injector fluid coupling and the cartridge fluid coupling are disconnected, and wherein the disposable cartridge is configured to be displaced relative to the disposable injector into a deployed configuration, in which the injector fluid coupling and the cartridge fluid coupling are in fluid communication; and a fastener configured to releasably fix the disposable delivery assembly in or relative to the receptacle, wherein the receptacle is configured to receive the disposable delivery assembly only when the disposable injector and the disposable cartridge are in the undeployed configuration and wherein the receptacle is shaped and configured to prevent insertion of the disposable delivery assembly into the receptacle when the disposable injector and the disposable cartridge are in the deployed configuration, and wherein the fastener is pivotably connected to the housing between an opened configuration and a closed configuration, wherein the receptacle is accessible in the opened configuration and wherein the receptacle is at least partially covered by the fastener in the closed configuration.

10. The drug delivery device according to claim 9, wherein the fastener is operably engageable with at least one of the disposable cartridge and the disposable injector and wherein the fastener is configurable from a release configuration into a locking configuration to mutually displace the disposable cartridge and the disposable injector into the deployed configuration.

11. The drug delivery device according to claim 10, wherein the fastener comprises a slider and wherein the fastener is configured to be transferred from the release configuration into the locking configuration by slidably displacing the slider from an extended position into a retracted position.

12. The drug delivery device according to claim 11, wherein the fastener comprises a pivotable lid with a free end formed by the slider, wherein in a closed configuration of the fastener, the slider at least partially encloses the disposable cartridge and is configured to be retracted from the extended position into the retracted position along a deploy direction, thereby displacing the disposable cartridge relative to the disposable injector into the deployed configuration.

13. The drug delivery device according to claim 9, wherein the fastener comprises a base portion pivotably mounted to the housing and wherein the base portion comprises a rear panel that extends radially from a pivot axis into the receptacle upon the fastener pivoting from the closed configuration towards the opened configuration.

14. The drug delivery device according to claim 9, wherein the fastener comprises a decoupler configured to engage with at least one of a stop member and a stop face of the disposable injector and the disposable cartridge when the fastener reaches the closed configuration.

15. A method of deploying or undeploying a disposable delivery assembly of a drug delivery device, the method comprising:

positioning the disposable delivery assembly against the drug delivery device, the disposable delivery assembly comprising:

a disposable injector comprising an injector base, an injection needle, a flexible tube, and an injector fluid coupling, wherein the injection needle is in fluid communication with the injector fluid coupling via the flexible tube, wherein the injector fluid coupling is fixed to the injector base; and a disposable cartridge comprising a reservoir at least partially filled with a liquid medicament and comprising a cartridge fluid coupling in fluid communication with the reservoir, wherein the disposable injector and the disposable cartridge are mechanically attached to each other in an undeployed configuration, in which the injector fluid coupling and the cartridge fluid coupling are disconnected, and wherein the disposable cartridge is configured to be displaced relative to the injector base into a deployed configuration, in which the injector fluid coupling and the cartridge fluid coupling are in fluid communication;

inserting a pre-assembly of the disposable cartridge and the disposable injector, in which the disposable cartridge and the disposable injector are in the undeployed configuration, in a receptacle of a housing of the drug delivery device, wherein one of the disposable cartridge and the disposable injector comprises at least one stop member engaging with a correspondingly shaped stop face of the other one of the disposable cartridge and the disposable injector and impedes a self-acting displacement of the disposable cartridge and the disposable injector from the undeployed configuration into the deployed configuration; and at least temporarily suspending a mutual abutment and engagement of the at least one stop member and the correspondingly shaped stop face by a decoupler of a fastener of the drug delivery device.

16. The method of claim 15, further comprising transferring the fastener from a locking configuration into a release configuration thereby inducing a displacement of the disposable cartridge relative to the disposable injector into the undeployed configuration.

* * * * *